United States Patent [19]

El-Nounou et al.

[11] Patent Number: 5,242,462
[45] Date of Patent: Sep. 7, 1993

[54] PERCUTANEOUS ANTI-MIGRATION VENA CAVA FILTER

[75] Inventors: Fozan O. El-Nounou, Billerica; Michael A. Savin, Norwood; Ronald A. Sahatjian, Lexington; Michael Weinreich, Acton; Thomas F. Kordis, Boston, all of Mass.

[73] Assignee: Boston Scientific Corp., Watertown, Mass.

[21] Appl. No.: 777,977

[22] Filed: Oct. 17, 1991

Related U.S. Application Data

[62] Division of Ser. No. 404,166, Sep. 7, 1989, Pat. No. 5,059,205.

[51] Int. Cl.[5] .............................. A61B 17/100
[52] U.S. Cl. ................................ 606/200; 210/448
[58] Field of Search .................. 606/195, 198, 200; 128/899; 210/448; 623/1, 12

[56] References Cited

U.S. PATENT DOCUMENTS 4,643,184 2/1987 Mobin-Uddin ............... 606/200

Primary Examiner—C. Fred Rosenbaum
Assistant Examiner—William Lewis
Attorney, Agent, or Firm—Don Halgren

[57] ABSTRACT

A filter device positionable within a blood vessel for trapping blood clots in that vessel, the filter device comprising a head with a plurality of divergent legs each secured at its proximal end, to the head, each leg having a hook arranged at its distal end.

Each leg has a radially outwardly directed radius of curvature to create a conical configuration to the filter assembly, while distributing the stress concentration along the length of the bend, so that the elastic limit of the material, stainless steel in this embodiment, is not exceeded, and which permits compact delivery of the filter, and adequate radially directed force to permit slight hook penetration of a vessel wall.

9 Claims, 4 Drawing Sheets

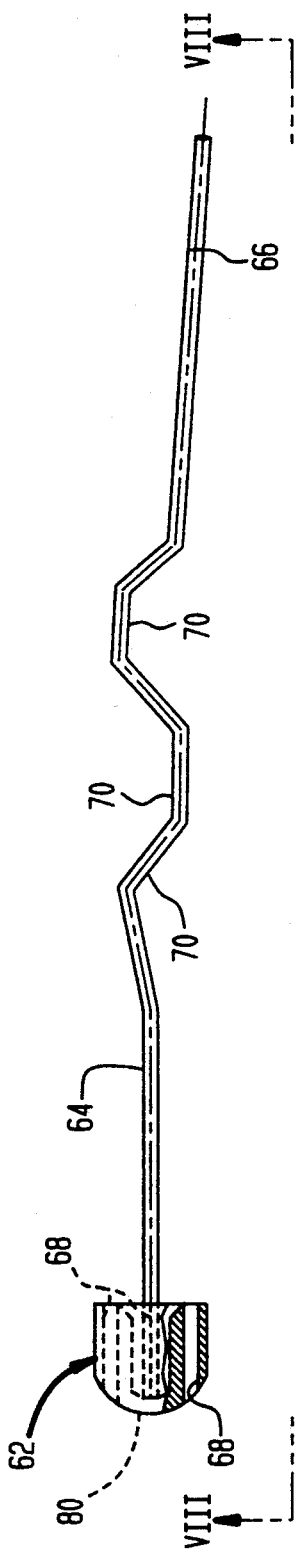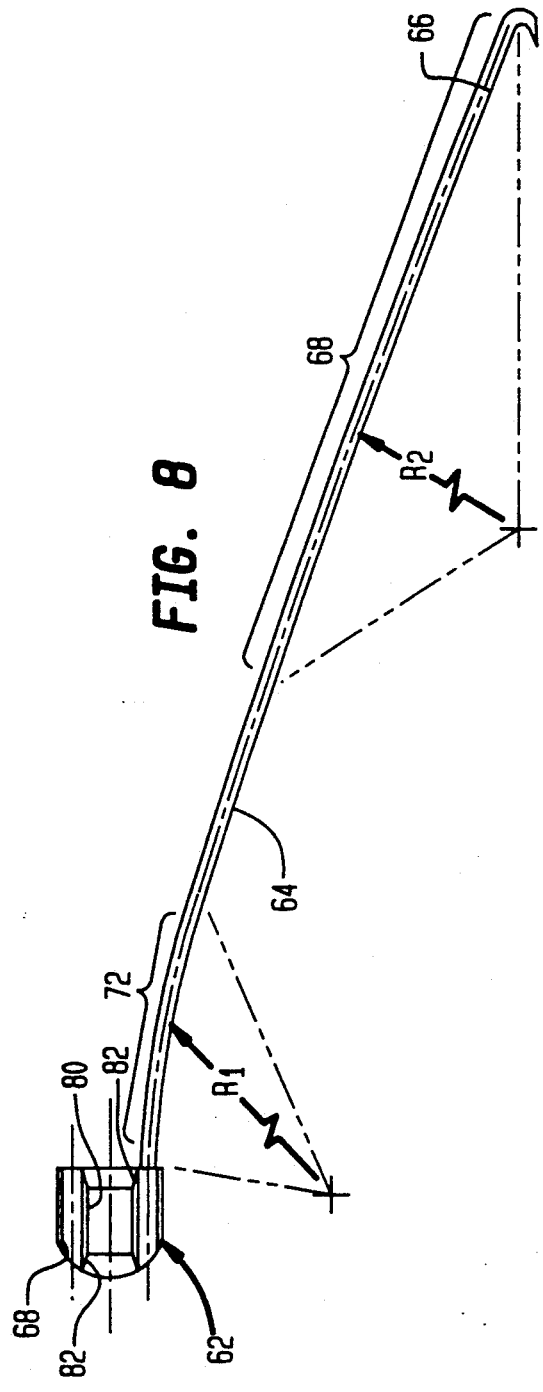

PERCUTANEOUS ANTI-MIGRATION VENA CAVA FILTER

This is a division of Ser. No. 07/404,166, filed Sept. 7, 1989, now U.S. Pat. No. 5,059,205.

BACKGROUND OF THE INVENTION

1. Field of the Invention

This invention relates to implantable blood filters and more particularly to vena cava filters which resist migration once they have been emplaced in a vessel.

2. Prior Art

Blood clots (emboli) carried in the blood stream often constitute serious threats to health and in some instances, to life itself. The reduction of such clots, or their stabilization and arrest of further migration in the circulatory system of the body, are desiderata constantly motivating the development by the medical profession of new techniques and devices for this purpose. Although emboli moving in other portions of the circulatory system can also present serious problems, development of means for preventing emboli from migrating into the pulmonary circulation from the vena cava has received the primary attention.

Ligation of the vena cava was an early technique to minimize movement of emboli therein, with collateral circulation being relied upon to provide adequate venous return of blood to the heart. This procedure, which involved major abdominal surgery, progressed to the utilization of harpstring filters; staple plication; smooth, serrated and channeling external clips evolving into intravascular springs; balloons; and filters. The utilization of filters emplaced in the vascular system provides the obvious advantage over ligation of major blood vessels such as the vena cava, of not requiring general anaesthesia surgery and laparotomy.

U.S. Pat. No. 3,540,431 discloses an intravascular filter for entrapment and arresting of emboli, advanced by Mobin-Uddin and associates. The Mobin-Uddin filter is an umbrella type structure which includes a plurality of expanding struts or ribs which carry points at the divergent ends thereof which impale or engage the vessel wall when the filter is in its expanded state. This device has had problems with migration, and it was withdrawn from the market in 1986.

U.S. Pat. No. 3,952,747 to Kimmell, Jr., incorporated, herein by reference, discloses a vena cava filter as well as a method and apparatus for percutaneous insertion of that filter into a human. The Kimmel disclosure defines the filter as having a plurality of convergent legs disposed in a generally conical array and joined at their convergent ends to an apical hub, each leg having a reversely bent hook at is distal end.

An advancement of the Kimmel, Jr. reference is shown in U.S. Pat. No. 4,817,600 to Herms et al., also incorporated herein by reference, which discloses a titanium filter having a plurality of legs joined to a head or nose bead, the legs having a first straight portion, and sharply divergent legs extending therefrom.

BRIEF SUMMARY OF THE INVENTION

The present invention features a filter of the Kimmell type having significant improvements to further minimize the likelihood of filter migration and to permit the filter to be emplaced through a small hole and into a vessel. In a first aspect of the invention, the filter of the type mentioned has a head, a plurality of legs attached to the head and divergent leg portions, each leg having securement means on its distal end with respect to the head, the improvement being that the securement means on the distal end of each leg being of multiple curvilinear configuration to define a pad which permits hook engagement of a vessel wall in which the filter is emplaced, while preventing penetration of that hook through the vessel wall, which might otherwise damage body tissue.

In a second or further aspect of the invention, the filter, which in this embodiment preferably is made from stainless steel, has a head with a plurality of legs extending distally therefrom, the head and legs having a centrally disposed longitude axis. The legs have proximal portions which are secured to the head, the proximal portions being generally parallel to the longitudinal axis to the filter. The legs have first portions closely distally adjacent to the head, which have a curvature therein, which geometry allows resilient deformation of the filter into the carrier, and subsequent resilient deformation when expelled from the carrier, so that the filter can end up as a general conical configuration of the legs with respect to the head of the filter. The legs also have a second portion distal to the first portion having a larger radius of curvature so as to permit a slight radial flaring of the hook ends of the legs when the filter is ejected out of its carrier, reducing the possibility of the hooks from becoming entangled with one another, while allowing the legs to be compressed radially inwardly, permitting the filter assembly to be placed into a smaller diameter carrier without stressing the stainless steel material of the legs beyond their elastic limit which would result in the filter having a smaller base diameter upon release from the carrier.

Another aspect of this invention involves the head having a central bore which is arranged co-axially with the longitudinal axis of the filter assembly. The central bore in the head is adapted to receive a guidewire during and after release of the filter assembly from its carrier as an aid for the alignment and centering of the filter assembly within a blood vessel during its implantation.

The first aspect of this invention more particularly involves the arrangement of the distalmost end of each leg defining a pad or landing, and spaced proximally therefrom, there is arranged a hook pointing outwardly from its respective leg in a manner generally normal thereto, and extending further radially outwardly from the longitudinal axis of the filter, than does the pad or landing thereadjacent, to permit the hook to engage the wall of the vessel, yet prevent deep penetration of the wall of the vessel by the hook and leg portions. Each pad or landing on the distalmost end of each leg is comprised of a reverse twisted segment of the wire of the leg, or a segment of the leg welded to the distalmost end and parallel thereto, the segment itself having the hook thereon, extending outwardly radially beyond the radially outwardmost portion of the pad or landing.

The second aspect of this invention more particularly involves the plurality of radially directed curves of each of the legs wherein the first radius of curvature for each leg begins closely distally adjacent the head of the filter, and defines an arc of about 0.5 inches in length with a radius of curvature of about 1.4 inches. The second radius of curvature for each leg extends across an arc about 1 inch in length along the distalmost portion of each leg, with a radius of curvature of about 8.4 inches, each leg being about 2.1 inches in total length. The first radius of curvature provides the generally conical aspect of the legs and head, while allowing delivery of the filter assembly through small holes and distributing the strain throughout the arc of the curve of the leg which is generated when the legs are collapsed into the small opening of the carrier, thus eliminating strains in excess of the yield strain, and the second radius of curvature being sufficient to keep the hooks from entangling with one another when the filter is ejected out its carrier device or during loading thereof, as shown in the aforementioned patent incorporated herewithin.

BRIEF DESCRIPTION OF THE DRAWINGS

The objects and advantages of the present invention will become more apparent when viewed in conjunction with the following drawings, in which:

FIG. 7 is a radially inwardly directed view upon one leg and the head of a vena cava filter; and FIG. 8 is a view taken along the lines VIII—VIII of FIG. 7, showing a further embodiment of the legs of a filter constructed according to the principles of the present invention.

DESCRIPTION OF THE PREFERRED EMBODIMENTS

Figure 1:
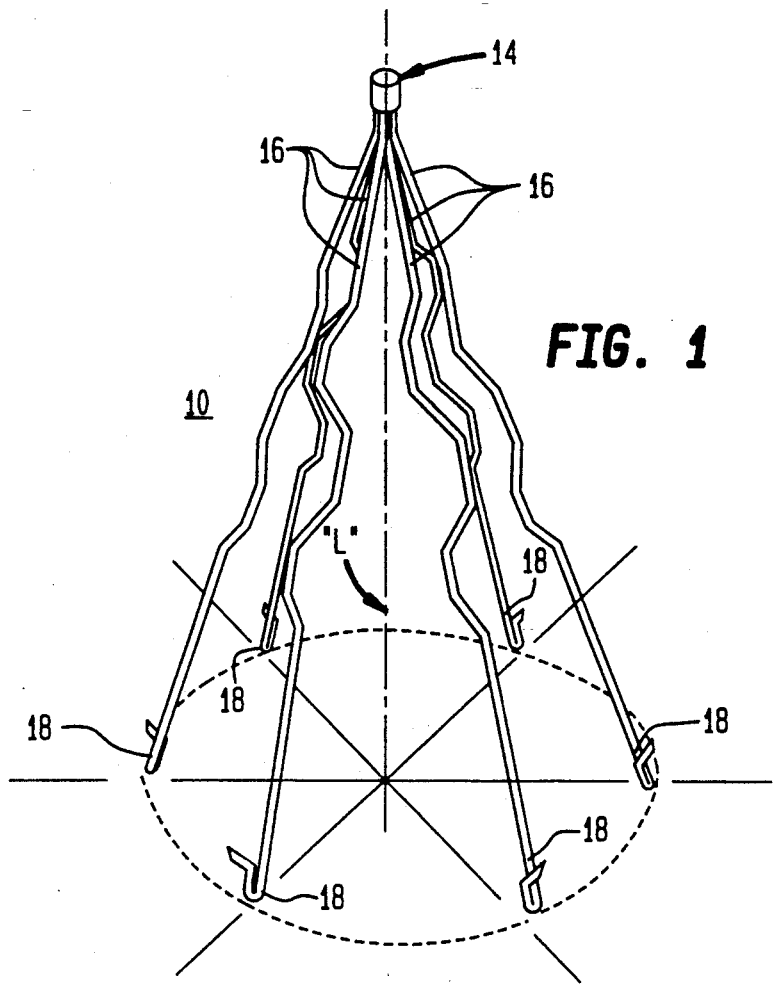
FIG. 1 is a perspective view of a vena cava filter showing the head and legs thereof in one embodiment of this invention.

Referring now to the drawings in detail, and particularly to FIG. 1, there is shown a first embodiment of a vena cava filter 10 having an apical hub or head 14 of generally cylindrical shape.

The filter 10 includes a plurality of elongated legs 16 which are of equal length, and are preferably identically configured to each other. The legs 16 are collectively arranged in a generally conical geometric configuration so that the legs 16 converge in the apical head 14, and are symmetrically spaced about a central longitudinally disposed axis "L", which is shown extending through the head 14, in FIG. 1. The legs are of equivalent diameter, being about 0.018 inches in diameter fabricated from stainless steel or titanium wire, and are of about 2.02 inches in final length. In the embodiment of the present invention, six legs are provided, however only one will be described in detail.

Figure 2:
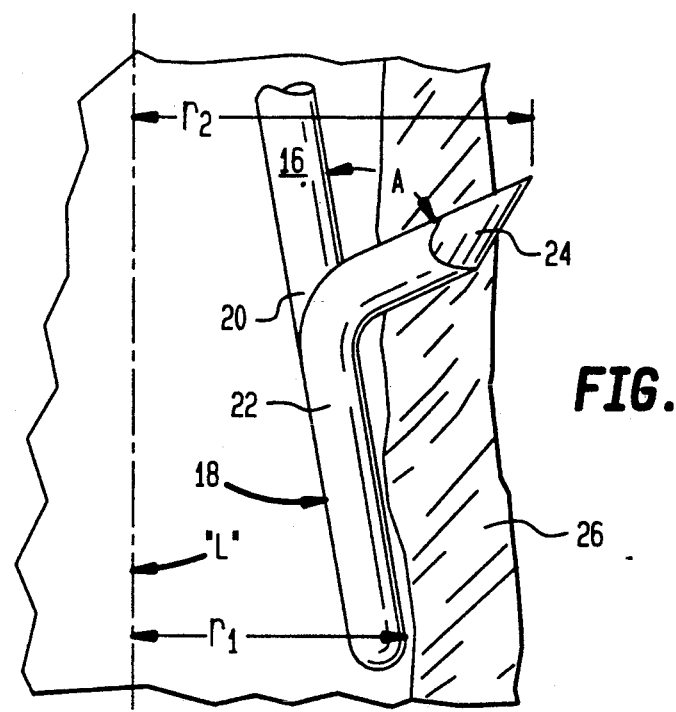
FIG. 2 is a side elevational view of the distal end of the preferred embodiment of one of the legs of a vena cava filter engaged with the cava wall.
Figure 3:
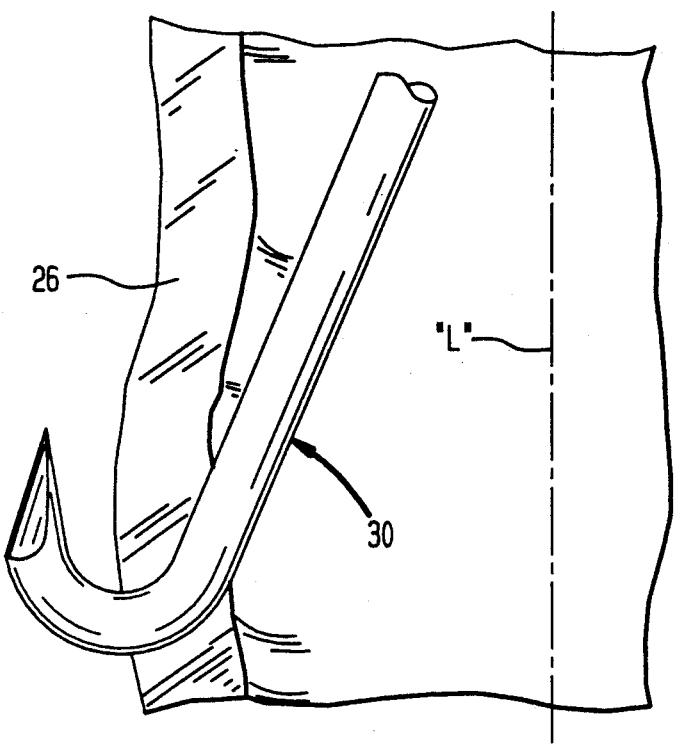
FIG. 3 is a side elevational view of the distal end of a leg of a prior art filter and the cava wall.

At its outermost end 18 which is distal with respect to the apical head 14, each leg 16 has a main portion 20 and a reversely bent portion 22 which is bent through an angle of about 180° in the plane which is tangential to the conical configuration of the legs, and is disposed parallel and contiguous to the main portion 20. A pointed tip portion 24 of the leg which comprises a hook, extends generally radially outwardly, away from the main portion 20 at an angle "A", as shown in FIG. 2 of from 70° to about 90°, preferably 80°; which tip portion 24 is shown piercing a cava wall 26. It is critical that the outwardly extending hook or tip portion 24 extend a greater radial dimension $r_2$ from the center line "L" of the filter 10 that the radial dimension $r_1$, which comprises the radius of the outermost end 18 from the center line "L". The contiguous main and reversibly bent portions 20 and 22 define a pad or landing which is caused to press against the inside of the cava wall 26, after the hook or tip portion 24 has pierced the cava wall 26, preventing penetration of the leg beyond the cava wall 26. This penetration, as shown by a prior art hook 30 in FIG. 3, may cause injury to the patient by movement of the hook 30 outside the cava wall 26. Without the distalmost portion of the leg comprising some form of landing, the hook may penetrate and slide directly through the cava wall. Without the hook or pointed end of the piercing element relatively normal to the wall surface, migration of the filter 10 may result, leading to extreme complications.

Figure 4:
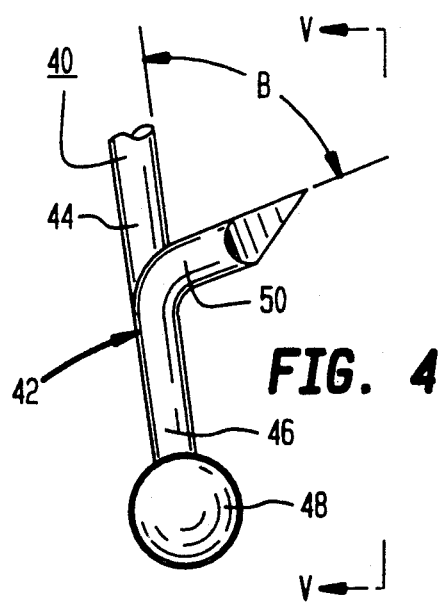
FIG. 4 is a side elevational view of a further embodiment of the distal end of a leg of a vena cava filter.
Figure 5:
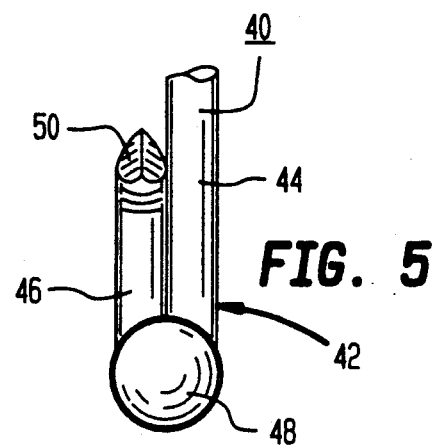
FIG. 5 is a view taken along the lines V—V of FIG. 4.

A further embodiment of the distal land or pad is shown in FIGS. 4 and 5, wherein a filter leg 40 has an outermost portion 42 comprised of an elongated main portion 44 and an attached segment 46, the distal ends of the attached segment 46 and the main portion 44 having a weld 48 to bind them together and preferably lie generally in the plane tangential to the conical configuration of the legs.

The attached segment 46 has a bent tip portion 50 or hook which is disposed at an angle "B" of about 70° to about 90°, preferably 80° with respect to the filter leg 40, as shown in FIG. 4. It is to be noted that the length of the tip portion 50 is similar to the tip portion 24 shown in FIG. 2, so that the end of the tip portion 50 is radially further from the longitudinal center line of the filter, than is the distalmost end (the weld 48 here) of the outermost portion 42 of the leg 40.

Figure 6:
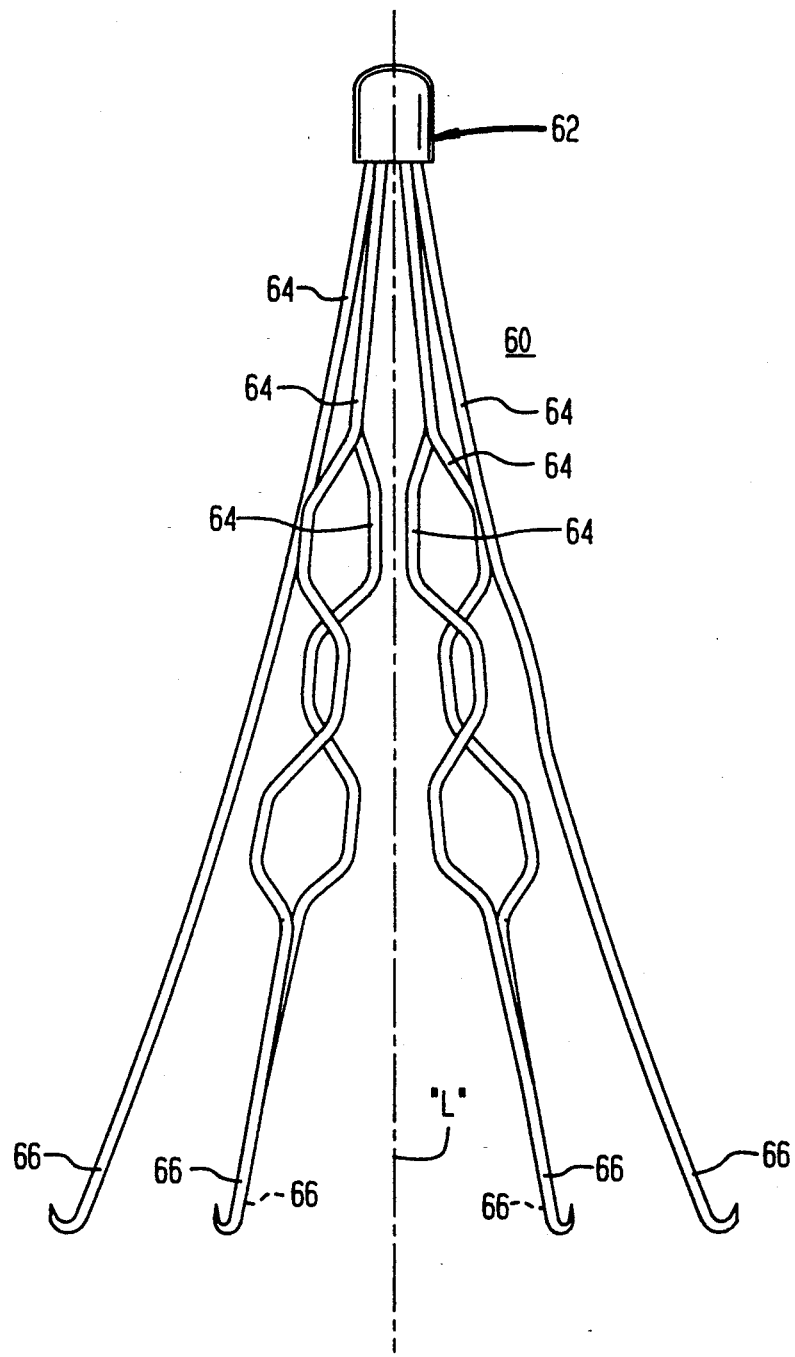
FIG. 6 is a perspective view of a vena cava filter showing the head and legs thereof of a further embodiment of this invention.

A further embodiment of a vena cava filter 60 is shown in FIG. 6 having an apical head 62, shown more particularly in FIGS. 7 and 8, The filter 60 includes a plurality of elongated legs 64 which are of equal length, and are configured identical to each other. The legs 64 are collectively arranged in a slightly outswept but generally conical configuration so that the legs 64 converge in the head 62, and are symmetrically spaced about a central longitudinally disposed axis "L", which is shown extending through the head 62 in FIG. 1. The legs are about 0.018 inches in diameter fabricated preferably from stainless steel, only one of the legs being described in detail.

Each leg has an outermost or distal end 66 with a hook configuration disposed thereon.

A typical leg 64 is shown further, in FIGS. 7 and 8, each mounted in a bore 68 in the apical head 62, which bore may be parallel to the center line of the filter 60. Each bore 68 receives only about 0.19 inches of the proximalmost end of each leg 64. When all the legs 64 are filling their proper respective bores 68, they are preferably welded therein. Each leg 64, in addition to having a plurality of U-shaped bends 70, disposed in the plane tangential to the cone defined by the legs 64, and intermediate their proximal and distal ends, as recited in the aforementioned incorporated patent, has a first slight bend 72 having a radius of curvature $R_1$ of about 1.4 inches arranged immediately adjacent the apical head 62, to cause the leg(s) 64 to flare radially outwardly about 18 degrees, thus defining their cone shaped configuration, which flare of only one leg 64 is best shown in FIG. 8. This flare permits the filter 60 to have enough elastic recoil to assume its general conical configuration, which is desirable to permit the filtration of blood clots while still allowing blood to flow around the captured clots, thus promoting dissolution of any clot and maintenance of vessel patency. The filter 60 with this flare can be passed through small delivery carriers without exceeding the elastic limit of the stainless steel filter legs 64. This maintenance of the stainless steel legs 64 within their elastic limits is critical to the stress free design, such that the filter 60 can be stored (in its carrier) in a collapsed mode yet have enough of a bend when it has been ejected into a vessel so that there is adequate radially outwardly directed force to permit the hooks to penetrate the caval wall upon the ejection of the filter 60.

A second slight bend 68 having a radius of curvature R2 of about 8.4 inches is disposed along the distal one inch of each leg 64 to provide a very slight, almost unnoticeable flare primarily for utilization in the filter carrier, now shown, so as to keep the hooks biased radially outwardly, and free from entanglement with one another while they are borne in and are ejected from their carrier.

The apical head 62 on the filter 60 has a central cylindrically shaped bore 80 (diam=0.046 inches, length of cylindrical portion 0.075 inches) which is adapted to receive inself aligning engagement, a guidewire (not shown). The bore 80 critically has its cylindrical portion which is in axial alignment with the longitudinal center line "L" of the filter 60. Each end of the bore 80 has a tapered counterbore 82 to permit access of a guidewire into the bore 82. This permits the filter 60 to be aligned and centered along the axis of a guidewire in a vessel during (and after) filter emplacement therein.

Thus there has been shown a vena cava filter having an apical hub from which extends a plurality of configured legs. The legs have a particular hook formation on their distal ends, which provides a landing or pad to prevent the hooks from sliding through the cava wall and injuring the patient thereby. The legs have a further configuration of a pair of outwardly directed curves to primarily create and preserve the general conical shape of the filter after insertion into a vessel through a small delivery hole, and secondarily provide a slight flare in the distal ends of each leg to prevent entanglement of their hooks as they are being moved to their ejection site in a patient.

What is claimed is:

1. A filter device positionable within a blood vessel, for trapping blood clots, comprising:
   an apical head;
   a plurality of divergent legs each secured at one of its ends to said head and each having securement means on its distal end with respect to said head;
   each of said legs having a first outwardly directed curvature immediately distally adjacent said head, said first curvature in each of said legs allowing insertion of the filter into a small diameter carrier, said first outwardly directed curvature extending in each of said legs, through an arc of about 0.5 inches:
   each of said legs having a second outwardly directed curvature in the distalmost portion thereof to provide a slight outwardly directed flare therein while said filter is borne in a carrier, to reduce the possibility of entanglement of the hooks.

2. A filter device as recited in claim 1, wherein said first outwardly directed curvature in each of said legs has a radius of curvature of about 1.4 inches.

3. A filter device as recited in claim 1, wherein said second outwardly directed bend in each of said legs extends through an arc of about 1 inch.

4. A filter device as recited in claim 3, wherein said second outwardly directed bend in each of said legs has a radius of curvature of about 8 inches.

5. A filter device for positioning within a blood vessel, to be utilized for entrapment of blood clots, said filter comprising;
   an apical head;
   a plurality of divergent legs each secured at one of its ends to said head and each having securement means on its distal end with respect to said head;
   each of said legs having a first outwardly directed curvature therein, closely distally adjacent said head, so that the distal remainder of said legs define a generically conical configuration and also to minimize the strain in said legs permitting the filter to be stored in a collapsed state, yet have enough elastic recoil to permit it to expand toward its uncollapsed configuration to allow penetration of a vessel wall upon ejection of the filter therein;
   said first outwardly directed bend extending in said legs through an arc of about 0.5 inches;
   said first outwardly directed bend having a radius of curvature of about 1.4 inches;
   said leg having a second outwardly directed curvature extending through an arc of about 1 inch.

6. A filter device as recited in claim 5, wherein said second outwardly directed curvature has a radius of curvature of about 8 inches.

7. A filter device positionable within a blood vessel for trapping blood clots, comprising:
   a apical head;
   a plurality of divergent legs each secured at one of its ends to said head and each having securement means on its distal end with respect to said head, said head and said legs having a longitudinally directed center line therewithin;
   said head having a cylindrical bore in axial alignment with said center line of said filter adaptable to receive a guidewire for alignment and guidance of said filter upon ejection thereof into a vessel;
   said cylindrical bore having a counterbore disposed in each longitudinal end thereof to facilitate emplacement of a guidewire therewith;
   said divergent legs having a first radially outwardly directed radius of curvature of about 1.4 inches over an arc of about 0.5 inches in length immediately adjacent said head to permit establishment of a conical geometric configuration to the plurality of legs extending from said apical head.

8. A filter device as recited in claim 7, wherein each of said divergent legs has a second radially outwardly directed radius of curvature of about 8 inches over an arc of about 1 inch in length at the distal end of said each leg, to create a slight outward flare therein, minimizing entanglement thereof.

9. A filter device as recited in claim 7, wherein said divergent legs are made from stainless steel.

* * * * *